United States Patent
Dishongh et al.

(10) Patent No.: US 8,304,849 B2
(45) Date of Patent: Nov. 6, 2012

(54) APPARATUS TO SEND BIOLOGICAL FLUIDS THROUGH A PRINTED WIRE BOARD

(75) Inventors: Terry Dishongh, Portland, OR (US); Bradford Needham, North Plains, OR (US); Kevin Rhodes, Beaverton, OR (US)

(73) Assignee: Intel Corporation, Santa Clara, CA (US)

( * ) Notice: Subject to any disclaimer, the term of this patent is extended or adjusted under 35 U.S.C. 154(b) by 1345 days.

(21) Appl. No.: 11/319,419

(22) Filed: Dec. 29, 2005

(65) Prior Publication Data
US 2007/0151942 A1 Jul. 5, 2007

(51) Int. Cl.
*H01L 31/0203* (2006.01)

(52) U.S. Cl. .......... 257/433; 257/397; 257/414; 216/13; 216/17

(58) Field of Classification Search ............ 216/13, 216/17, 18, 83; 174/250, 252, 262, 257; 438/460, 462; 257/287, 397, 414, 433, 537, 257/678, 713
See application file for complete search history.

(56) References Cited

U.S. PATENT DOCUMENTS

| | | | |
|---|---|---|---|
| 6,282,782 B1 * | 9/2001 | Biunno et al. | 29/852 |
| 6,515,235 B2 * | 2/2003 | Moller | 174/256 |
| 6,821,819 B1 * | 11/2004 | Benavides et al. | 438/122 |
| 2003/0045019 A1 * | 3/2003 | Kubena | 438/49 |
| 2005/0118705 A1 * | 6/2005 | Rabbitt et al. | 435/287.1 |
| 2005/0287789 A1 * | 12/2005 | Tunaboylu | 438/622 |

* cited by examiner

*Primary Examiner* — Lan Vinh
(74) *Attorney, Agent, or Firm* — Pillsbury Winthrop Shaw Pittman LLP

(57) ABSTRACT

A device containing a printed wire board (PWB), wherein the PWB comprises a fluid channel, wherein the fluid channel is a closed channel having a noble metal-containing layer on a surface of the fluid channel is disclosed. A method of making a device containing providing a substrate of a PWB; and fabricating a fluid channel in the PWB, wherein the fluid channel is a closed channel having a noble meal-containing layer on a surface of the fluid channel is disclosed. Also, a method containing providing a printed wire board (PWB), wherein the PWB comprises a fluid channel, wherein the fluid channel is a closed channel having a noble metal-containing layer on a surface of the fluid channel, and flowing fluid the fluid channel is disclosed.

47 Claims, 3 Drawing Sheets

APPARATUS TO SEND BIOLOGICAL FLUIDS THROUGH A PRINTED WIRE BOARD

RELATED APPLICATIONS

None.

FIELD OF INVENTION

The embodiments of the invention relate to an apparatus to send a fluid, e.g., a biological fluid, through a printed wire board (PWB). The embodiments of the invention could be used, for example, for methods and devices for cooling the PWB or for complex data collection and analysis in biomolecule detection. The invention transcends several scientific disciplines such as polymer chemistry, biochemistry, molecular biology, medicine and medical diagnostics.

BACKGROUND

The molecular-level origins of disease are being elucidated at a rapid pace, potentially ushering in a new era of personalized medicine in which a specific course of therapy is developed for each patient. To fully exploit this expanding knowledge of disease phenotype, new methods for detecting multiple biomolecules (e.g., DNA and proteins) by microelectromechanical systems (MEMS) devices mounted on a PWB are being developed. The biomolecule detection methods must be rapid, sensitive, and capable of diagnosing cellular phenotype in vivo or ex vivo in the MEMS devices, which require getting an organic fluid containing the cellular phenotype, e.g., a biological fluid, to the MEMS devices. However, one issue in getting the biological fluid to MEMS devices mounted on a PWB is providing a clean channel through the PWB to deliver the biological fluid to the MEMS. The embodiments of this invention provide, for example, a novel non-obvious apparatus to deliver biological fluids to MEMS sensors.

DETAILED DESCRIPTION

Figure 1:
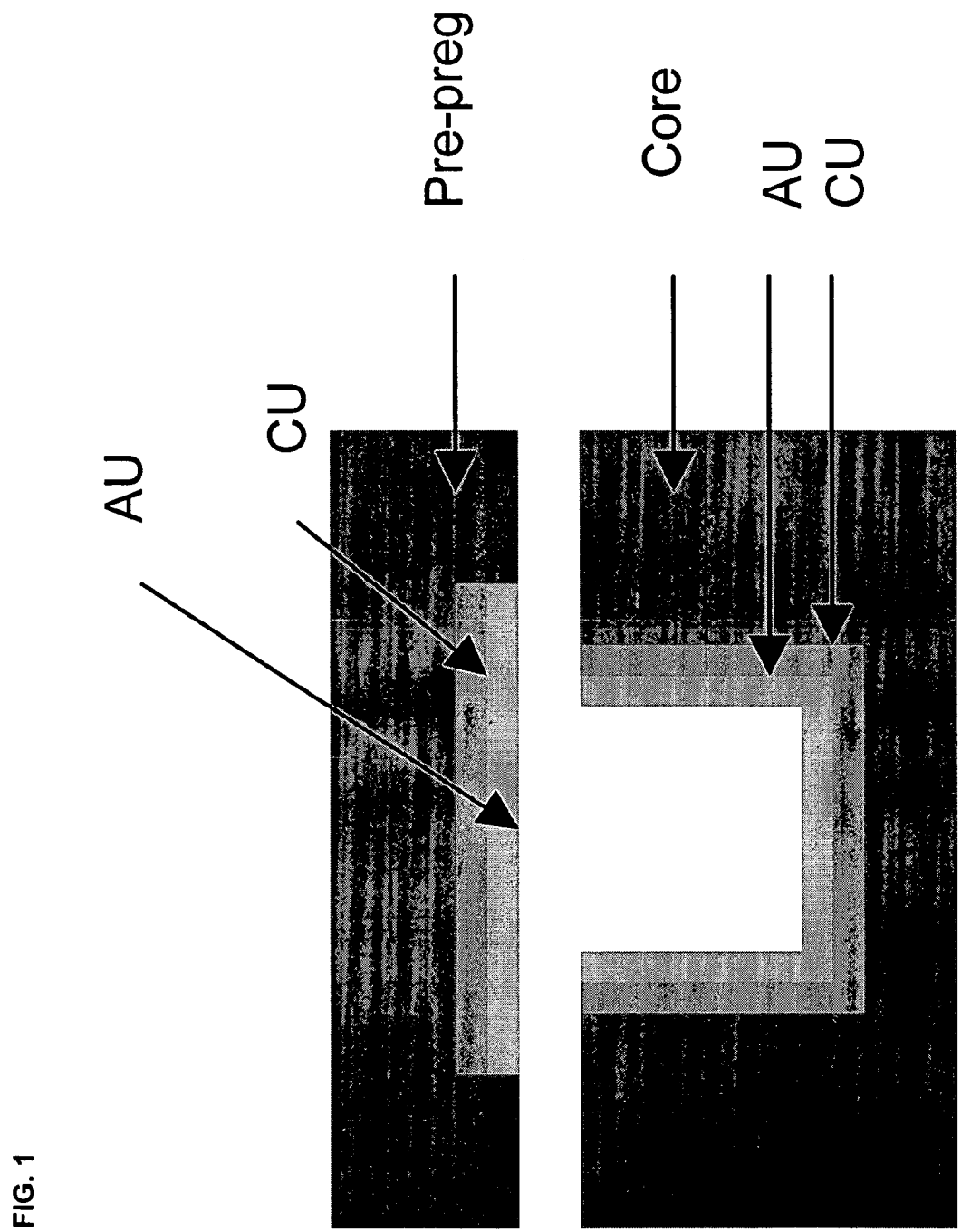
FIG. 1 shows a schematic of a PWB of the embodiments of the invention with a fluid channel therein.

A biological fluid (or biofluid) sample often contains many thousands or even more types of biomolecules and clinical diagnosis needs to measure multiple analytes for disease confirmation. The embodiments of the invention allow for single or multiple analyte detection by one or more MEMS devices mounted on a PWB having a closed fluid channel to deliver the biological fluid to the MEMS devices.

Analytes include nucleic acids (DNA and RNA), which can form double-stranded molecules by hybridization, that is, complementary base pairing. The specificity of nucleic acid hybridization is such that the detection of molecular and/or nanomaterials binding events can be done through electrical readout of polarization changes caused by the interaction of charged target molecules (DNA, RNA, proteins, for example) and chemically modified nanomaterials (carbon nanotubes, nanowires, nanoclusters functionalized with DNA, for example) with complementary molecular probes (DNA, RNA, anti-body, for example) attached to the electrodes (such as Au, Pt, for example). This specificity of complementary base pairing also allows thousands of hybridization to be carried out simultaneously in the same experiment on a MEMS device.

The practice of the embodiments of the invention may employ, unless otherwise indicated, techniques of organic chemistry, polymer technology, molecular biology (including recombinant techniques), cell biology, biochemistry, and immunology, which are within the skill of the art. Such techniques include polymer array synthesis, hybridization, ligation, detection of hybridization using a label. Specific illustrations of suitable techniques can be had by reference to the example herein below. However, other equivalent procedures can, of course, also be used.

As used in the specification and claims, the singular forms "a", "an" and "the" include plural references unless the context clearly dictates otherwise. For example, the term "an array" may include a plurality of arrays unless the context clearly dictates otherwise.

The term "noble metal" refers to a metal or alloy that is highly resistant to oxidation and corrosion. Examples include gold, silver, tantalum, platinum, palladium and combinations thereof.

The term "printed wire board (PWB)" or "printed circuit board" refer to a conductive pattern of wiring paths and component pads bonded to an insulated base material or substrate. One of the purposes of the PWB is to physically support and electrically interconnect the components and hardwire assembled upon it. The PWB of embodiments of the invention could comprise a copper foil glued to an insulated base material for conductive patterns and pads known as traces, foils, and donuts. The foil thickness generally determines the capacity the PWB, which is typically rated in ounce per square inch. The foil or foils could be on a single side or both sides of the PWB. The foils could also be multilayered. The PWB could either be rigid or flexible. The rigid PWB could comprise a rigid laminate comprising, for example, paper pulp and phenolic resin glue, fiberglass and epoxy resin, or Teflon and polyester resin. The flexible PWB could comprise a Mylar ribbon sandwich, for example. The PWB could include a wafer, a semiconductor, a scribe line, a via, a metal line, a capacitor, a transistor, a FET, a CMOS, a microcoil, an electrode, a microchip, an integrated circuit (IC), a closed channel, a waveguide, a microprocessor, a die, an array (a microarray or a macroarray), a biochip, among others.

The term "wafer" means a semiconductor substrate. A wafer could be fashioned into various sizes and shapes. It could be used as a substrate for a microchip. The substrate could be overlaid or embedded with circuitry, for example, a pad, via, an interconnect or a scribe line. The circuitry of the wafer could also serve several purposes, for example, as microprocessors, memory storage, and/or communication capabilities. The circuitry can be controlled by the microprocessor on the wafer itself or controlled by a device external to the wafer.

The term "semiconductor" refers to a substance (usually a solid chemical element or compound) that can conduct electricity under some conditions but not others, making it a good medium for the control of electrical current. Its conductance varies depending on the current or voltage applied to a control electrode, or on the intensity of irradiation by infrared (IR), visible light, ultraviolet (UV), or X rays. The specific properties of a semiconductor depend on the impurities, or dopants, added to it. An N-type semiconductor carries current mainly in the form of negatively-charged electrons, in a manner similar to the conduction of current in a wire. A P-type semiconductor carries current predominantly as electron deficiencies called holes. A hole has a positive electric charge, equal and opposite to the charge on an electron. In a semiconductor material, the flow of holes occurs in a direction opposite to the flow of electrons. Elemental semiconductors include antimony, arsenic, boron, carbon, germanium, selenium, silicon, sulfur, and tellurium. Silicon is the best-known of these, forming the basis of most integrated circuits (ICs). Common semiconductor compounds include gallium arsenide, indium antimonide, and the oxides of most metals. Of these, gallium arsenide is widely used in low-noise, high-gain, weak-signal amplifying devices.

A "scribe line" is typically an "inactive" area between the active dies that provide area for separating the die (usually with a saw). Often, metrology and alignment features populate this area.

A "via" refers to a hole etched in the interlayer of a dielectric which is then filled with an electrically conductive material, preferably tungsten, to provide vertical electrical connection between stacked up interconnect metal lines that are capable of conducting electricity.

"Metal lines" within a die are interconnect lines. Metal interconnect lines do not typically cross the scribe line boundary to electrically connect two dies or, as in the some embodiments of this invention, a multitude of die to one or more wafer pads.

The term "capacitor" refers to an electric circuit element used to store charge, and generally comprising two metallic plates separated and insulated from each other by a dielectric.

The term "transistor" refers to an electronic device containing a semiconductor and having at least three electrical contacts, and generally used in a circuit as an amplifier, detector, or switch. A transistor regulates current or voltage flow and acts as a switch or gate for electronic signals. A transistor generally has three layers of a semiconductor material, each capable of carrying a current. The semiconductor material is given special properties by a chemical process called doping. The doping results in a material that either adds extra electrons to the material (which is then called N-type for the extra negative charge carriers) or creates "holes" in the material's crystal structure (which is then called P-type because it results in more positive charge carriers). The transistor's three-layer structure contains an N-type semiconductor layer sandwiched between P-type layers (a PNP configuration) or a P-type layer between N-type layers (an NPN configuration). A small change in the current or voltage at the inner semiconductor layer (which acts as the control electrode) produces a large, rapid change in the current passing through the entire component. The component can thus act as a switch, opening and closing an electronic gate many times per second. Transistors are generally the basic elements in integrated circuits, which could contain very large numbers of transistors interconnected with circuitry and baked into a single silicon microchip or chip.

The term "field effect transistor" (FET) is a family of transistors that rely on an electric field to control the conductivity of a "channel" in a semiconductor material. FETs, like all transistors, can be thought of as voltage-controlled resistors. Most FETs could be made using bulk semiconductor processing techniques, using the single-crystal semiconductor wafer as the active region, or channel.

The term "CMOS" means complementary metal oxide semiconductor. CMOS generally uses two complementary transistors per gate (one with N-type material; the other with P-type material). When one transistor is maintaining a logic state, it requires almost no power.

A "microcoil" refers to a localized microelectromagnet on or in a solid support which is, was, or is intended to be used for the formation of a selected molecule under the influence of magnetic field. Integrated microcoils in an array may have any convenient shape, e.g., circular, rectangular, elliptical, wedge-shaped, etc. In some embodiments of the invention, the microcoil could be smaller than about 1 $cm^2$ or less than 1 $mm^2$, and still more preferably less than 0.5 $mm^2$. In most preferred embodiments the microcoil could have an area less than about 10,000 $\mu m^2$ or, more preferably, less than 100 $\mu m^2$. For independent magnetic field control, each microcoil is connected to its own on-chip current source. The operating principle of the microcoil array for cell manipulation is to create and move magnetic field peaks by modulating currents in the microcoils. For instance, by activating only one microcoil in the array, a magnetic bead suspended in fluid will be attracted to the field peak at the center of the microcoil on the surface of the IC having the microcoil. Subsequently, by turning off the microcoil while activating an adjacent one, the magnetic field peak is moved to the center of the adjacent microcoil, transporting the magnetic bead to the new peak location. The spatial resolution of the manipulation is determined by the spacing between two neighboring coils. For precise spatial control of individual magnetic beads, the microcoil could be carefully designed to generate a single magnetic field peak on the chip surface. Note that while the microcoil generally produces a single magnetic peak on the chip surface, multiple magnetic peaks can exist below the surface.

An "electrode" is a body or a location at which an electrochemical reaction occurs. The term "electrochemical" refers to an interaction or interconversion of electric and chemical phenomena. A "functionalized electrode" is an electrode of a microchip array having a probe molecule that has a specific chemical affinity to a target molecule. An "unfunctionalized electrode" is an electrode of a microchip array having no probe molecule or having a probe molecule that has no specific chemical affinity to a target molecule.

The electrodes used in embodiments of the invention may be composed of, but are not limited to, metals such as iridium and/or platinum, and other metals, such as, palladium, gold, silver, copper, mercury, nickel, zinc, titanium, tungsten, aluminum, as well as alloys of various metals, and other conducting materials, such as, carbon, including glassy carbon, reticulated vitreous carbon, basal plane graphite, edge plane graphite and graphite. Doped oxides such as indium-tin oxide and semiconductors such as silicon oxide and gallium arsenide are also contemplated. Additionally, the electrodes may be composed of conducting polymers, metal doped polymers, conducting ceramics and conducting clays. Among the metals, platinum and palladium are especially preferred because of the advantageous properties associated with their ability to absorb hydrogen, i.e., their ability to be "preloaded" with hydrogen before being used in the methods of the invention.

The electrodes may be connected to an electric source in any known manner. Preferred ways of connecting the electrodes to the electric source include CMOS (complementary metal oxide semiconductor) switching circuitry, radio and microwave frequency addressable switches, light addressable switches, direct connection from an electrode to a bond pad on the perimeter of a semiconductor chip, and combinations thereof. CMOS switching circuitry involves the connection of each of the electrodes to a CMOS transistor switch. The switch could be accessed by sending an electronic address signal down a common bus to SRAM (static random access memory) circuitry associated with each electrode. When the switch is "on", the electrode is connected to an electric source. Radio and microwave frequency addressable switches involve the electrodes being switched by a RF or microwave signal. This allows the switches to be thrown both with and/or without using switching logic. The switches can be tuned to receive a particular frequency or modulation frequency and switch without switching logic. Light addressable switches are switched by light. In this method, the electrodes can also be switched with and without switching logic. The light signal can be spatially localized to afford switching without switching logic. This could be accomplished, for example, by scanning a laser beam over the electrode array; the electrode being switched each time the laser illuminates it.

The term "microchip" refers to a unit of packaged circuitry (usually called an integrated circuit) that is generally, but not necessarily, manufactured from a material such as silicon at a very small scale. Microchips could include both program logic and/or memory. Microchips could be used for computers and for special purposes such as analog-to-digital conversion, bit slicing, and gateways.

The term "integrated circuit" (IC) refers to a semiconductor wafer on which plurality of tiny resistors, capacitors, and/or transistors are fabricated. An IC can function as an amplifier, oscillator, timer, counter, computer memory, or microprocessor. A particular IC is categorized as either linear (analog) or digital, depending on its intended application.

The term "closed channel" refers to a conduit enclosed with one or more walls that prevent passage of a fluid across the walls of the conduit. For example, the closed channel could be pipe having a circular cross-section or could be shaped like a duct having a substantially rectangular cross-section.

The term "waveguide" refers to a device that controls the propagation of an electromagnetic wave so that the wave is forced to follow a path defined by the physical structure of the guide. Generally speaking, the electric and magnetic fields of an electromagnetic wave have a number of possible arrangements when the wave is traveling through a waveguide. Each of these arrangements is known as a mode of propagation. Optical waveguides are used at optical frequencies. An "optical waveguide" is any structure having the ability to guide optical energy. Optical waveguides may be (a) thin-film deposits used in integrated optical circuits (IOCs) or (b) optical fibers.

"Microprocessor" is a processor on an integrated circuit (IC) chip. The processor may be one or more processor on one or more IC chip. The chip is typically a silicon chip with thousands of electronic components that serves as a central processing unit (CPU) of a computer or a computing device.

The terms "die," "polymer array chip," "DNA array," "array chip," "DNA array chip," or "biochip" are used interchangeably and refer to a collection of a large number of probes arranged on a shared substrate which could be a portion of a silicon wafer, a nylon strip or a glass slide.

An "array" is an intentionally created collection of molecules which can be prepared either synthetically or biosynthetically. The molecules in the array can be identical or different from each other. The array can assume a variety of formats, e.g., libraries of soluble molecules; libraries of compounds tethered to resin beads, silica chips, or other solid supports. The array could either be a macroarray or a microarray, depending on the size of the sample spots on the array. A macroarray generally contains sample spot sizes of about 300 microns or larger and can be easily imaged by gel and blot scanners. A microarray would generally contain spot sizes of less than 300 microns.

"Predefined region," "spot" "binding area" or "pad" refers to a localized area on a solid support which is, was, or is intended to be used for the formation of a selected molecule and is otherwise referred to herein in the alternative as a "selected" region. The predefined region may have any convenient shape, e.g., circular, rectangular, elliptical, wedge-shaped, etc. For the sake of brevity herein, "predefined regions" are sometimes referred to simply as "regions" or "spots." In some embodiments, a predefined region and, therefore, the area upon which each distinct molecule is synthesized is smaller than about 1 $cm^2$ or less than 1 $mm^2$, and still more preferably less than 0.5 $mm^2$. In most preferred embodiments the regions have an area less than about 10,000 $\mu m^2$ or, more preferably, less than 100 $\mu m^2$. Additionally, multiple copies of the polymer will typically be synthesized within any preselected region. The number of copies can be in the thousands to the millions. More preferably, a die of a wafer contains at least 400 spots in, for example, an at least 20×20 matrix. Even more preferably, the die contains at least 2048 spots in, for example, an at least 64×32 matrix, and still more preferably, the die contains at least 204,800 spots in, for example, an at least 640×320 array. A spot could contain an electrode to generate an electrochemical reagent, a working electrode to synthesize a polymer and a confinement electrode to confine the generated electrochemical reagent. The electrode to generate the electrochemical reagent could be of any shape, including, for example, circular, flat disk shaped and hemisphere shaped. In some aspects, a predefined region can be achieved by physically separating the regions (i.e., beads, resins, gels, etc.) into wells, trays, etc.

"Solid support," "support," and "substrate" refer to a material or group of materials having a rigid or semi-rigid surface or surfaces. In some aspects, at least one surface of the solid support will be substantially flat, although in some aspects it may be desirable to physically separate synthesis regions for different molecules with, for example, wells, raised regions, pins, etched trenches, or the like. In certain aspects, the solid support(s) will take the form of beads, resins, gels, microspheres, or other geometric configurations.

The term "target" or "target molecule" refers to a molecule of interest that is to be analyzed, e.g., a nucleotide, an oligonucleotide, a polynucleotide, a peptide, or a protein. The target or target molecule could be a small molecule, biomolecule, or nanomaterial such as but not necessarily limited to a small molecule that is biologically active, nucleic acids and their sequences, peptides and polypeptides, as well as nano-structure materials chemically modified with biomolecules or small molecules capable of binding to molecular probes such as chemically modified carbon nanotubes, carbon nanotube bundles, nanowires, nanoclusters or nanoparticles. The target molecule may be fluorescently labeled DNA or RNA.

The term "probe" or "probe molecule" refers to a molecule that binds to a target molecule for the analysis of the target. The probe or probe molecule is generally, but not necessarily, has a known molecular structure or sequence. The probe or probe molecule is generally, but not necessarily, attached to the substrate of the array. The probe or probe molecule is typically a nucleotide, an oligonucleotide, a polynucleotide, a peptide, or a protein, including, for example, cDNA or pre-synthesized polynucleotide deposited on the array. Probes molecules are biomolecules capable of undergoing binding or molecular recognition events with target molecules. (In some references, the terms "target" and "probe" are defined opposite to the definitions provided here.) The polynucleotide probes require only the sequence information of genes, and thereby can exploit the genome sequences of an organism. In cDNA arrays, there could be cross-hybridization due to sequence homologies among members of a gene family. Polynucleotide arrays can be specifically designed to differentiate between highly homologous members of a gene family as well as spliced forms of the same gene (exon-specific). Polynucleotide arrays of the embodiment of this invention could also be designed to allow detection of mutations and single nucleotide polymorphism. A probe or probe molecule can be a capture molecule.

Molecular probes could be immobilized on the surface of individually addressable electrode arrays of the MEMS device through the surface functionalization techniques. Electrodes allow polarization changes to be electrically detected. The polymer arrays of the embodiment of the invention could be a DNA array (collections of DNA probes on a shared base) comprising a dense grid of spots (often called elements or pads) arranged on a miniature support. Each spot could represent a different gene.

The probe is usually hybridized with a complex RNA or cDNA target generated by making DNA copies of a complex mixture of RNA molecules derived from a particular cell type (source). The composition of such a target reflects the level of individual RNA molecules in the source. The intensities of the signals resulting from the binding events from the DNA spots of the DNA chip after hybridization between the probe and the target represent the relative expression levels of the genes of the source.

The term "capture molecule" refers to a molecule that is immobilized on a surface. The capture molecule is generally, but not necessarily, binds to a target or target molecule. The capture molecule is typically a nucleotide, an oligonucleotide, a polynucleotide, a peptide, or a protein, but could also be a small molecule, biomolecule, or nanomaterial such as but not necessarily limited to a small molecule that is biologically active, nucleic acids and their sequences, peptides and polypeptides, as well as nanostructure materials chemically modified with biomolecules or small molecules capable of binding to a target molecule that is bound to a probe molecule to form a complex of the capture molecule, target molecule and the probe molecule. The capture molecule may be fluorescently labeled DNA or RNA. The capture molecule may or may not be capable of binding to just the target molecule or just the probe molecule.

"Binding" refers to an interaction between two or more substances, such as between a target and a capture or probe molecule, that results in a sufficiently stable complex so as to permit detection of the bound molecule complex. In certain embodiments of the invention, binding may also refer to an interaction between a second molecule and a target.

"Associated with" or "association" refers to a direct or indirect interactions between two or more substances, such as between a target and a capture or probe molecule, that results in a sufficiently stable complex. For example, a molecule or complex of molecules is "associated with" the surface of a substrate when the molecule or complex is either bound to the surface of the substrate directly, through another molecule or substance, or to both. In other words, substances are "associated with" each other when any one member of the substances is directly bound to at least another member of the substances.

The terms "label" and "tag" are used interchangeably to refer to a marker or indicator distinguishable by the observer but not necessarily by the system used to identify an analyte or target. Labels are often used in biological assays to be conjugated with, or attached to, an otherwise difficult to detect substance. At the same time, Labels usually do not change or affect the underlining assay process. A label or tag used in biological assays include, but not limited to, a radioactive material, a magnetic material, quantum dot, an enzyme, a liposome-based label, a chromophore, a fluorophore, a dye, a nanoparticle, a composite-organic-inorganic nano-cluster, a colloidal metal particle, or a combination thereof.

The term "sequence" refers to the particular ordering of monomers within a macromolecule and it may be referred to herein as the sequence of the macromolecule.

The term "hybridization" refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." For example, hybridization refers to the formation of hybrids between a probe polynucleotide (e.g., a polynucleotide of the invention which may include substitutions, deletion, and/or additions) and a specific target polynucleotide (e.g., an analyte polynucleotide) wherein the probe preferentially hybridizes to the specific target polynucleotide and substantially does not hybridize to polynucleotides consisting of sequences which are not substantially complementary to the target polynucleotide. However, it will be recognized by those of skill that the minimum length of a polynucleotide desired for specific hybridization to a target polynucleotide will depend on several factors: G/C content, positioning of mismatched bases (if any), degree of uniqueness of the sequence as compared to the population of target polynucleotides, and chemical nature of the polynucleotide (e.g., methylphosphonate backbone, phosphorothiolate, etc.), among others.

Methods for conducting polynucleotide hybridization assays have been well developed in the art. Hybridization assay procedures and conditions will vary depending on the application and are selected in accordance with the general binding methods known in the art.

It is appreciated that the ability of two single stranded polynucleotides to hybridize will depend upon factors such as their degree of complementarity as well as the stringency of the hybridization reaction conditions.

As used herein, "stringency" refers to the conditions of a hybridization reaction that influence the degree to which polynucleotides hybridize. Stringent conditions can be selected that allow polynucleotide duplexes to be distinguished based on their degree of mismatch. High stringency is correlated with a lower probability for the formation of a duplex containing mismatched bases. Thus, the higher the stringency, the greater the probability that two single-stranded polynucleotides, capable of forming a mismatched duplex, will remain single-stranded. Conversely, at lower stringency, the probability of formation of a mismatched duplex is increased.

The appropriate stringency that will allow selection of a perfectly-matched duplex, compared to a duplex containing one or more mismatches (or that will allow selection of a particular mismatched duplex compared to a duplex with a higher degree of mismatch) is generally determined empirically. Means for adjusting the stringency of a hybridization reaction are well-known to those of skill in the art.

The term "molecule" generally refers to a chemical made up of two or more atoms and includes a macromolecule, biomolecule or polymer as described herein. However, arrays comprising single molecules, as opposed to macromolecules or polymers, are also within the scope of the embodiments of the invention.

The term "monomer" refers to those monomers that are used to a form a polymer. However, the meaning of the monomer will be clear from the context in which it is used. The monomers in a given polymer or macromolecule can be identical to or different from each other. A monomer can be a small or a large molecule, regardless of molecular weight. Furthermore, each of the monomers may be protected members which are modified after synthesis.

The monomers for forming the polymers of the embodiments of the invention, e.g., a polymeric brush or a linker molecule, have for example the general structure:

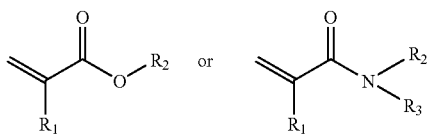

wherein $R_1$ is hydrogen or lower alkyl; $R_2$ and $R_3$ are independently hydrogen, or —Y—Z, wherein Y is lower alkyl, and Z is hydroxyl, amino, or C(O)—R, where R is hydrogen, lower alkoxy or aryloxy.

The term "alkyl" refers to those groups such as methyl, ethyl, propyl, butyl etc, which may be linear, branched or cyclic.

The term "alkoxy" refers to groups such as methoxy, ethoxy, propoxy, butoxy, etc., which may be linear, branched or cyclic.

The term "lower" as used in the context of lower alkyl or lower alkoxy refers to groups having one to six carbons.

The term "aryl" refers to an aromatic hydrocarbon ring to which is attached an alkyl group. The term "aryloxy" refers to an aromatic hydrocarbon ring to which is attached an alkoxy group. One of ordinary skill in the art would readily understand these terms.

Other monomers for preparing macromolecules of the embodiments of the invention are well-known in the art. For example, when the macromolecule is a peptide, the monomers include, but are not restricted to, for example, amino acids such as the L-amino acids, the D-amino acids, and the synthetic and/or natural amino acids. When the macromolecule is a nucleic acid, or polynucleotide, the monomers include any nucleotide. When the macromolecule is a polysaccharide, the monomers can be any pentose, hexose, heptose, or their derivatives.

A "polymer" comprises two or more monomers covalently joined. The monomers may be joined one at a time or in strings of multiple monomers, ordinarily known as "oligomers." Thus, for example, one monomer and a string of five monomers may be joined to form a macromolecule or polymer of six monomers. Similarly, a string of fifty monomers may be joined with a string of hundred monomers to form a macromolecule or polymer of one hundred and fifty monomers. The term polymer as used herein includes, for example, both linear and cyclic polymers of nucleic acids, polynucleotides, polynucleotides, polysaccharides, oligosaccharides, proteins, polypeptides, peptides, phospholipids and peptide nucleic acids (PNAs). The peptides include those peptides having either α-, β-, or ω-amino acids. In addition, polymers include heteropolymers in which a known drug is covalently bound to any of the above, polyurethanes, polyesters, polycarbonates, polyureas, polyamides, polyethyleneimines, polyarylene sulfides, polysiloxanes, polyimides, polyacetates, or other polymers which will be apparent upon review of this disclosure.

A "macromolecule" refers to large molecule having many smaller structural units linked together. A macromolecule could be a polymer or a protein, for example.

The term "nucleotide" includes deoxynucleotides and analogs thereof. These analogs are those molecules having some structural features in common with a naturally occurring nucleotide such that when incorporated into a polynucleotide sequence, they allow hybridization with a complementary polynucleotide in solution. Typically, these analogs are derived from naturally occurring nucleotides by replacing and/or modifying the base, the ribose or the phosphodiester moiety. The changes can be tailor-made to stabilize or destabilize hybrid formation, or to enhance the specificity of hybridization with a complementary polynucleotide sequence as desired, or to enhance stability of the polynucleotide.

The term "polynucleotide" or "nucleic acid" as used herein refers to a polymeric form of nucleotides of any length, either ribonucleotides or deoxyribonucleotides, that comprise purine and pyrimidine bases, or other natural, chemically or biochemically modified, non-natural, or derivatized nucleotide bases. Polynucleotides of the embodiments of the invention include sequences of deoxyribopolynucleotide (DNA), ribopolynucleotide (RNA), or DNA copies of ribopolynucleotide (cDNA) which may be isolated from natural sources, recombinantly produced, or artificially synthesized. A further example of a polynucleotide of the embodiments of the invention may be polyamide polynucleotide (PNA). The polynucleotides and nucleic acids may exist as single-stranded or double-stranded. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. The polymers made of nucleotides such as nucleic acids, polynucleotides and polynucleotides may also be referred to herein as "nucleotide polymers.

An "oligonucleotide" is a polynucleotide having 2 to 20 nucleotides. Phosphoramidites protected in this manner are known as FOD phosphoramidites.

Analogs also include protected and/or modified monomers as are used in polynucleotide synthesis. As one of skill in the art is well aware, polynucleotide synthesis uses a variety of base-protected nucleoside derivatives in which one or more of the nitrogens of the purine and pyrimidine moiety are protected by groups such as dimethoxytrityl, benzyl, tert-butyl, isobutyl and the like.

A "nanomaterial" as used herein refers to a structure, a device or a system having a dimension at the atomic, molecular or macromolecular levels, in the length scale of approximately 1-500 nanometer range. Preferably, a nanomaterial has properties and functions because of the size and can be manipulated and controlled on the atomic level. Examples of a nanomaterial include a carbon nanotube and fullerene.

A "carbon nanotube" refers to a fullerene molecule having a cylindrical or toroidal shape. A "fullerene" refers to a form of carbon having a large molecule consisting of an empty cage of sixty or more carbon atoms.

The term "biomolecule" refers to any organic molecule that is part of a living organism. A "complex of a biomolecule" refers to a structure made up of two or more types of biomolecules. Examples of a complex of biomolecule include a cell or viral particles. A cell can include bacteria, fungi, animal mammalian cell, for example.

The term "biofluid" or "biological fluid" refers to a fluid comprising a biomolecule. Biofluids can be excreted (such as urine or sweat), secreted (such as breast milk or bile), obtained with a needle (such as blood or cerebrospinal fluid), or develop as a result of a pathological process such as (such as blister or cyst fluid). The biofluids of the embodiments of the invention could include an antibody, a peptide, a protein, a carbohydrate, a lipid, an antigen, a ligand, an analyte, a reporter, a Raman-active organic compound, among others, for example.

An "antibody" is any of various bodies or substances in the blood which act in antagonism to harmful foreign bodies, as toxins or the bacteria producing the toxins. Normal blood serum apparently contains various antibodies, and the introduction of toxins or of foreign cells also results in the development of their specific antibodies. For example, an antibody is a Y-shaped protein on the surface of B cells that is secreted into the blood or lymph in response to an antigenic stimulus, such as a bacterium, virus, parasite, or transplanted organ, and that neutralizes the antigen by binding specifically to it; an immunoglobulin.

A "peptide" is a polymer in which the monomers are amino acids and which are joined together through amide bonds and alternatively referred to as a polypeptide. In the context of this specification it should be appreciated that the amino acids may be the L-optical isomer or the D-optical isomer. Peptides are two or more amino acid monomers long and often more than 20 amino acid monomers long.

A "protein" is a long polymer of amino acids linked via peptide bonds and which may be composed of two or more polypeptide chains. More specifically, the term "protein" refers to a molecule composed of one or more chains of amino acids in a specific order; for example, the order as determined by the base sequence of nucleotides in the gene coding for the protein. Proteins are essential for the structure, function, and regulation of the body's cells, tissues, and organs, and each protein has unique functions. Examples are hormones, enzymes, and antibodies.

A "carbohydrate" is a compound with carbon, hydrogen and oxygen usually in a proportion to form water with the general formula $C_n(H_2O)_n$. Carbohydrates can also be called chemically as neutral compounds of carbon, hydrogen and oxygen. Carbohydrates are mainly sugars and starches, together constituting one of the three principal types of nutrients used as energy sources (calories) by the body. Carbohydrates come in simple forms such as sugars and in complex forms such as starches and fiber. The body breaks down most sugars and starches into glucose, a simple sugar that the body can use to feed its cells. Complex carbohydrates are derived from plants. Dietary intake of complex carbohydrates can lower blood cholesterol when they are substituted for saturated fat. Carbohydrates are classified into mono, di, tri, poly and heterosaccharides. The smallest carbohydrates are monosaccharides such as glucose whereas polysaccharides such as starch, cellulose and glycogen can be large and even indeterminate in length.

A "lipid" is defined as a substance such as a fat, oil or wax that dissolves in alcohol but not in water. Lipids contain carbon, hydrogen and oxygen but have far less oxygen proportionally than carbohydrates. Lipids are an important part of living cells. Together with carbohydrates and proteins, lipids are the main constituents of plant and animal cells. Cholesterol and triglycerides are lipids. Lipids are easily stored in the body. They serve as a source of fuel and are an important constituent of the structure of cells. Lipids include fatty acids, neutral fats, waxes and steroids (like cortisone). Compound lipids (lipids complexed with another type of chemical compound) comprise the lipoproteins, glycolipids and phospholipids.

An "antigen" a substance that is capable of causing the production of an antibody. For example, when an antigen is introduced into the body, it stimulates the production of an antibody. Antigens include toxins, bacteria, foreign blood cells, and the cells of transplanted organs.

A "ligand" is a molecule that is recognized by a particular receptor. Examples of ligands that can be investigated by this invention include, but are not restricted to, agonists and antagonists for cell membrane receptors, toxins and venoms, viral epitopes, hormones, hormone receptors, peptides, enzymes, enzyme substrates, cofactors, drugs (e.g. opiates, steroids, etc.), lectins, sugars, polynucleotides, nucleic acids, oligosaccharides, proteins, and monoclonal antibodies. Ligands to cells or cell-derived molecules, which can include both known and unknown ligands as well as putative drug candidates that are either unattached to other solid supports or attached to surfaces or particle-like structures, could interact with other cell-derived molecules in a manner such that binding between two binding partners occurs and can be detected. One of the binding partners or its attached support can additionally be derivatized with a substance that can be recognized and quantified by a detection apparatus. This complex (through interaction) is then brought into the presence of the detection apparatus using characteristics of the associated complex that differentiate it from the unassociated binding partners.

A "receptor" is molecule that has an affinity for a given ligand. Receptors may-be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. However, as the term receptor is used herein, no difference in meaning is intended. A "ligand receptor pair" is formed when two macromolecules have combined through molecular recognition to form a complex. Other examples of receptors which can be investigated by this invention include but are not restricted to:

a) Microorganism receptors: Determination of ligands which bind to receptors, such as specific transport proteins or enzymes essential to survival of microorganisms, is useful in developing a new class of antibiotics. Of particular value would be antibiotics against opportunistic fungi, protozoa, and those bacteria resistant to the antibiotics in current use.

b) Enzymes: For instance, one type of receptor is the binding site of enzymes such as the enzymes responsible for cleaving neurotransmitters; determination of ligands which bind to certain receptors to modulate the action of the enzymes which cleave the different neurotransmitters is useful in the development of drugs which can be used in the treatment of disorders of neurotransmission.

c) Antibodies: For instance, the invention may be useful in investigating the ligand-binding site on the antibody molecule which combines with the epitope of an antigen of interest; determining a sequence that mimics an antigenic epitope may lead to the-development of vaccines of which the immunogen is based on one or more of such sequences or lead to the development of related diagnostic agents or compounds useful in therapeutic treatments such as for auto-immune diseases (e.g., by blocking the binding of the "anti-self" antibodies).

d) Nucleic Acids: Sequences of nucleic acids may be synthesized to establish DNA or RNA binding sequences.

e) Catalytic Polypeptides: Polymers, preferably polypeptides, which are capable of promoting a chemical reaction involving the conversion of one or more reactants to one or more products. Such polypeptides generally include a binding site specific for at least one reactant or reaction intermediate and an active functionality proximate to the binding site, which functionality is capable of chemically modifying the bound reactant.

f) Hormone receptors: Examples of hormones receptors include, e.g., the receptors for insulin and growth hormone. Determination of the ligands which bind with high affinity to a receptor is useful in the development of, for example, an oral replacement of the daily injections which diabetics take to relieve the symptoms of diabetes. Other examples are the vasoconstrictive hormone receptors; determination of those ligands which bind to a receptor may lead to the development of drugs to control blood pressure.

g) Opiate receptors: Determination of ligarids which bind to the opiate receptors in the brain is useful in the development of less-addictive replacements for morphine and related drugs.

The term "analyte" refers to any molecule or compound. An analyte can be in the solid, liquid, gaseous or vapor phase. By "gaseous or vapor phase analyte" is meant a molecule or compound that is present, for example, in the headspace of a liquid, in ambient air, in a breath sample, in a gas, or as a contaminant in any of the foregoing. It will be recognized that the physical state of the gas or vapor phase can be changed by pressure, temperature as well as by affecting surface tension of a liquid by the presence of or addition of salts etc.

The term analyte further includes polynucleotide analytes such as those polynucleotides defined below. These include m-RNA, r-RNA, t-RNA, DNA, DNA-RNA duplexes, etc. The term analyte also includes receptors that are polynucleotide binding agents, such as, for example, peptide nucleic acids (PNA), restriction enzymes, activators, repressors, nucleases, polymerases, histones, repair enzymes, chemotherapeutic agents, and the like.

The analyte may be a molecule found directly in a sample such as a body fluid from a host. The sample can be examined directly or may be pretreated to render the analyte more readily detectable. Furthermore, the analyte of interest may be determined by detecting an agent probative of the analyte of interest such as a specific binding pair member complementary to the analyte of interest, whose presence will be detected only when the analyte of interest is present in a sample. Thus, the agent probative of the analyte becomes the analyte that is detected in an assay. The body fluid can be, for example, urine, blood, plasma, serum, saliva, semen, stool, sputum, cerebral spinal fluid, tears, mucus, and the like.

The analyte can further be a member of a specific binding pair (sbp) and may be a ligand, which is monovalent (monoepitopic) or polyvalent (polyepitopic), usually antigenic or haptenic, and is a single compound or plurality of compounds which share at least one common epitope or determinant site. The analyte can be a part of a cell such as bacteria or a cell bearing a blood group antigen such as A, B, D, etc., or an HLA antigen or a microorganism, e.g., bacterium, fungus, protozoan, or virus. Also, the analyte could be charged. A member of a specific binding pair ("sbp member") is one of two different molecules, having an area on the surface or in a cavity which specifically binds to and is thereby defined as complementary with a particular spatial and polar organization of the other molecule. The members of the specific binding pair are referred to as ligand and receptor (antiligand) or analyte and probe. Therefore, a probe is a molecule that specifically binds an analyte. These will usually be members of an immunological pair such as antigen-antibody, although other specific binding pairs such as biotin-avidin, hormones-hormone receptors, nucleic acid duplexes, IgG-protein A, polynucleotide pairs such as DNA-DNA, DNA-RNA, and the like are not immunological pairs but are included in the invention and the definition of sbp member. Bioanalyte can also be complex of molecules or compounds in organized or random fashion, such cells, virus, bacteria, fungi, etc.

The term "reporter" means a detectable moiety. The reporter can be detected, for example, by Raman spectroscopy. Generally, the reporter and any molecule linked to the reporter can be detected without a second binding reaction. The reporter can be COIN (composite-organic-inorganic nanocluster), magnetic-COIN, quantum dots, and other Raman or fluorescent tags, for example.

The term "COIN" refers to a composite-organic-inorganic nanocluster(s). The COIN could be surface-enhanced Raman spectroscopy (SERS)-active nanoclusters incorporated into a gel matrix and used in certain other analyte separation techniques described herein. COINs are composite organic-inorganic nanoclusters. These SERS-active probe constructs comprise a core and a surface, wherein the core comprises a metallic colloid comprising a first metal and a Raman-active organic compound. The COINs can further comprise a second metal different from the first metal, wherein the second metal forms a layer overlying the surface of the nanocluster. The COINs can further comprise an organic layer overlying the metal-containing layer, which organic layer comprises the probe. Suitable probes for attachment to the surface of the SERS-active nanoclusters include, without limitation, antibodies, antigens, polynucleotides, oligonucleotides, receptors, ligands, and the like.

As used herein, "Raman-active organic compound" refers to an organic molecule that produces a unique SERS signature in response to excitation by a laser. A variety of Raman-active organic compounds are contemplated for use as components in COINs. In certain embodiments, Raman-active organic compounds are polycyclic aromatic or heteroaromatic compounds. Typically the Raman-active organic compound has a molecular weight less than about 300 Daltons.

Additional, non-limiting examples of Raman-active organic compounds useful in COINs include TRIT (tetramethyl rhodamine isothiol), NBD (7-nitrobenz-2-oxa-1,3-diazole), Texas Red dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, 5-carboxy-2',4',5',7'-tetrachlorofluorescein, 5-carboxyfluorescein, 5-carboxy rhodamine, 6-carboxyrhodamine, 6-carboxytetramethyl amino phthalocyanines, azomethines, cyanines, xanthines, succinylfluoresceins, aminoacridine, and the like.

In certain embodiments, the Raman-active compound is adenine, adenine, 4-amino-pyrazolo(3,4-d)pyrimidine, 2-fluoroadenine, N6-benzolyadenine, kinetin, dimethyl-allyl-amino-adenine, zeatin, bromo-adenine, 8-aza-adenine, 8-azaguanine, 6-mercaptopurine, 4-amino-6-mercaptopyrazolo(3,4-d)pyrimidine, 8-mercaptoadenine, or 9-amino-acridine 4-amino-pyrazolo(3,4-d)pyrimidine, or 2-fluoroadenine. In one embodiment, the Raman-active compound is adenine.

"Micro-Electro-Mechanical Systems (MEMS)" include the integration of mechanical elements, sensors, actuators, or electronics on a common silicon substrate through microfabrication technology. The MEMS device could also include an array or a biochip. MEMS often combine electrical and mechanical functionalities on a single substrate. An example of a MEMS device could be a small mechanical chamber where two liquids (biofluids, drugs, chemicals etc.) are mixed and a sensor interprets the results. MEMS could also be integrated with logic functionalities i.e. having a CMOS circuit to perform some algorithm with the data provided by the sensor. The CMOS circuit could then have circuit elements that transport the results of the algorithm and the sensor input to another device (i.e. output to further devices comprising the overall micro-system). While the electronics are fabricated using integrated circuit (IC) process sequences (e.g., CMOS, Bipolar, or BICMOS processes), the micromechanical components could be fabricated using compatible "micromachining" processes that selectively etch away parts of the silicon wafer or add new structural layers to form the mechanical and electromechanical devices. Microelectronic integrated circuits can be thought of as the "brains" of a system and MEMS augments this decision-making capability with "eyes" and "arms" to allow microsystems to sense and control the environment. Sensors gather information from the environment through measuring mechanical, thermal, biological, chemical, optical, and magnetic phenomena. The electronics then process the information derived from the sensors and through some decision making capability direct the actuators to respond by moving, positioning, regulating, pumping, and filtering, thereby controlling the environment for some desired outcome or purpose. Because MEMS devices are generally manufactured using batch fabrication techniques similar to those used for integrated circuits, unprecedented levels of functionality, reliability, and sophistication can be placed on a small silicon chip at a relatively low cost.

A "micro-channel" is a channel, groove, or conduit having at least one dimension in the micrometer ($\mu$m), or less than $10^{-3}$ meter (mm), scale. Although micro-channels are typically straight along their length, they may contain angles and curves of different degrees along their length. Although the micro-channels typically have rectangular cross-sections, they may also have other shapes of cross-sections, such as circle. The micro-channels are usually suitable for fluidic communications, such as carrying through a biological liquid. The micro-channels are often part of an integrated device, such a microfluidic device or an integrated circuit such that liquid flowing through the micro-channels are in a controlled pattern and able to be analyzed as desired.

One of the mechanical processes of the MEMS embodiments of the invention is transporting small amounts of fluids through micro-channels, which are also called "microfluidic channels." These fluid channels are preferably embedded in a covering layer. One example of a microfluidic channel used in MEMS could be an electrokinetic pump. Electrokinetic pumps use an ionic fluid and a current imposed at one end of the fluid channel and collected at the other end of the fluid channel. This current in the ionic fluid impels the ionic fluid through the electrokinetic pump.

A "microfluidic device" is a device that has one or more micro-channels. A microfluidic device may be part of an integrated device, such as an integrated separation or detection equipment or an integrated circuit. Fluids used in microfluidic devices include whole blood samples, bacterial cell suspensions, protein or antibody solutions and various buffers and saline. Microfluidic devices can be used to obtain many interesting measurements, including fluid mechanical properties, cellular and molecular diffusion coefficients, fluid viscosity, pH values, chemical and biological binding coefficients and enzyme reaction kinetics. Other applications for microfluidic devices include cell and molecule detection and separation, capillary electrophoresis, isoelectric focusing, immunoassays, flow cytometry, sample injection of proteins for analysis via mass spectrometry, DNA analysis, cell manipulation, and cell separation. In the embodiment of the invention, magnetic materials and technologies are incorporated into the microfluidic devices for applications such as cell and biomolecule detection and separation.

The use of microfluidic devices to conduct biomedical assays has many significant advantages. First, because the volume of fluids within these channels is very small, usually several nano-liters, the amount of reagents and analytes required for the assays is quite small. This is especially significant for expensive reagents. The fabrications techniques used to construct microfluidic devices, discussed in more details herein, are relatively inexpensive and are very amenable both to highly elaborated, multiplexed devices and also to mass production, such as in an integrated circuit die. In manners similar to that for microelectronics, microfluidic technologies also enable the fabrication of highly integrated devices for performing different functions on the same substrate chip. Embodiments of the invention helps create integrated, portable clinical diagnostic devices for home and bedside use, thereby eliminating time consuming laboratory analysis procedures.

In the embodiments of the invention, the flow of a fluid through a microfluidic channel, or micro-channel, can be characterized by the Reynolds number (Re), defined as $$Re = LV_{avg}\rho/\mu$$

where L is the most relevant length scale, $\mu$ is the fluid viscosity, $\rho$ is the fluid density, and $V_{avg}$ is the average velocity of the flow. For many micro-channels, including channels with a substantially rectangular cross-section, L is equal to 4A/P where A is the cross-sectional area of the channel and P is the wetted perimeter of the channel. Due to the small dimensions of micro-channels, the Re is usually much less than 100, often less than 1.0. In this Reynolds number regime, flow is completely laminar and no turbulence occurs. The transition to turbulent flow generally occurs in the range of Reynolds number 2000. Laminar flow provides a means by which molecules can be transported in a relatively predictable manner through micro-channels.

The term "prepreg" refers to resin pre-impregnated fibers. The prepregs of the embodiments of the invention could include a variety of resins and fibers. For example, the fibers include glass, graphite, aramid, ceramic, polyolefin and metallized fibers. The resins could thermosetting resins such as polyesters, epoxies, phenolics, polyimdes, bismalemides, or a thermoplastic resin. The prepregs of the embodiments of this invention could be made in a variety of ways including impregnation of fibers by solution impregnation, e.g., by dipping the fiber in solution containing a resin, or by a hot melt impregnation, e.g., by coating the fibers with a film of the resin or passing the fibers through a heated resin bath tank. The prepregs could also be made by impregnating a resin powder on the fibers or by electrostatically depositing a powder of a resin on the fibers.

The embodiments of the invention relate to a device comprising a printed wire board (PWB), wherein the PWB comprises a fluid channel, wherein the fluid channel is a closed channel comprising a noble metal-containing layer on a surface of the fluid channel. Preferably, the PWB further comprises a biochip, an integrated circuit, a microchip, a semiconductor device, a MEMS device and the fluid channel is positioned to permit a fluid to flow through the fluid channel to the MEMS device, wherein the MEMS device is a MEMS sensor, microfluidic device. In one variation, the fluid channel is a substantially circular pipe or a substantially rectangular duct. Preferably, the fluid channel has a cross-sectional dimension to permit a biofluid to flow through the fluid channel. Preferably, the fluid channel has a cross-sectional dimension of about 1 micron to about 1.5 cm. In one variation, the PWB further comprises a cured prepreg and the fluid channel is at least partially in the cured prepreg. Preferably, the fluid channel further comprises copper-containing layer and the noble metal-containing layer comprises gold. In the context of a fluid flowing through the fluid channel, the surface of the fluid channel is a surface where the fluid that flows through the fluid channel touches the fluid channel. Generally, the fluid channel has at least two openings for fluidic communication.

In one variation of the embodiments of the invention, the fluid channel is a micro-channel. Preferably, the micro-channel comprises at least one straight segment comprising a cross-section comprising a rectangle. Preferably, the rectangle has a height and a width of between about 1.0 μm and about 500 μm. More preferably, the rectangle has a height and a width of between 10 μm and 50 μm. In yet another embodiment of the invention, a device in the PWB could further comprise an inlet fluid reservoir in fluid communication with at least one of the openings of the fluid channel; and an outlet fluid reservoir in fluid communication with at least one of the openings of the fluid channel.

Yet other embodiments of the invention relate to a method of making a device comprising providing a substrate of a printed wire board (PWB); and fabricating a fluid channel in the PWB, wherein the fluid channel is a closed channel comprising a noble metal-containing layer on a surface of the fluid channel. Preferably, the fabricating the fluid channel comprises creating an uncapped channel in the substrate and applying a cap layer on the uncapped channel to form the closed channel. Preferably, the substrate comprises a prepreg and the cap layer is a prepreg. Preferably, the fabricating the fluid channel further comprises depositing a metal-containing layer within the uncapped channel. Preferably, the metal-containing layer comprises copper, the metal-containing layer comprises a copper-containing layer and a gold-containing layer, or the metal-containing layer comprises a noble metal, wherein the noble metal is selected from the group consisting of gold, silver, tantalum, platinum, palladium and combinations thereof.

In one variation of the embodiments of the invention, the method of making the device further comprises curing the prepregs of the substrate and the cap layer. Preferably, the prepregs comprise a fiber-reinforced thermosetting resin material. Preferably, the PWB comprises a device selected from the group consisting of a biochip, an integrated circuit, a microchip, a semiconductor device, a MEMS device and combinations thereof. Preferably, the fabricating the fluid channel comprises a subtractive process. Alternatively, the fabricating the fluid channel comprises an additive process. In one variation, the fabricating the fluid channel comprises a combination of a subtractive process and an additive process. Preferably, the subtractive process is selected from a group consisting of a photographic process, a laser ablation process, a screen printing process, and combinations thereof. Preferably, the additive process comprises providing the substrate without a conductive plating, fabricating the uncapped channel in the substrate, applying the cap layer on the uncapped channel to form the closed channel, applying a reverse-pattern mask on the substrate or the cap layer, and depositing a conductive pattern. The method could further comprise removing the reverse pattern from the substrate or the cap layer. Preferably, the fabricating the fluid channel comprises a lithography process, wherein the lithography process is selected, for example, from the group consisting of near-field phase shift lithography, replica molding, micromolding in capillaries, micro-transfer molding, solvent-assisted microcontact molding, microcontact printing and combinations thereof.

Yet other embodiments of the invention relate to a method comprising providing a printed wire board (PWB), wherein the PWB comprises a fluid channel, wherein the fluid channel is a closed channel comprising a noble metal-containing layer on a surface of the fluid channel, and flowing a fluid through the fluid channel. Preferably, the method further comprises cooling the PWB or comprises delivering the fluid to a device in the PWB, or both. Preferably, the device is selected from the group consisting of a biochip, an integrated circuit, a microchip, a semiconductor device, a MEMS device and combinations thereof. Preferably, the fluid flowing though the fluid channel comprises a biological fluid, wherein the biological fluid comprises a salt. Generally, the noble metal-containing layer substantially prevents migration of the salt through the noble metal-containing layer. In one variation, the fluid channel could be used for delivering a fluid to at least two devices in the PWB.

The PWB of the embodiments of the invention could be manufactured by a plurality of processes, among them being the subtractive (etching) and the additive (plating) processes. The subtractive process could be primarily used for prototype production while the additive process could be used for mass production.

Among the subtractive processes, there are three possible processes: (1) photographic (2) laser ablation and (3) screen printing.

1) Photographic Method—Copper clad circuit board is coated with a light sensitive material (photo resist), then a photographic mask of the PWB layout is placed on the copper clad and exposed to a UV light source to burn image into photo resist. Next, PWB is chemically sprayed/dipped with a special developer to remove un-exposed photo resist. PWB is then sprayed or dipped in acid to remove the unwanted copper. Finally PWB is chemically stripped to remove exposed resist on remaining copper.
2) Laser ablation—This process is substantially similar to the photographic method except that instead of the PWB being sprayed by an acid and etched, it is etched by laser.
2) Screening Method—Copper clad circuit board has PWB layout inked on it thru a silk screening process (similar to T-shirts). Next, PWB is chemically sprayed/dipped in acid to remove the unwanted copper. Finally PWB is chemically stripped to remove silk screened ink on remaining copper.

The additive process of the embodiments of the invention could start with providing the substrate without a conductive plating, fabricating the fluid channel in the substrate, applying the cap layer on the channel to form the closed channel, applying a reverse-pattern mask on the substrate or the cap layer, and depositing a conductive pattern. In addition, tooling and component holes could also be drilled or punched prior to applying the cap layer or after applying the cap layer to the substrate. The reverse-pattern mask could be deposited on the substrate or the cap layer through electrolysis. The reverse pattern could then be stripped off from the PWB.

The device of the embodiments of the invention could also be made by using soft lithography method with poly-dimethyl siloxane. With these techniques it is possible to generate patterns with critical dimensions as small as 30 nm. These techniques use transparent, elastomeric polydimethylsiloxane (PDMS) "stamps" with patterned relief on the surface to generate features. The stamps can be prepared by casting prepolymers against masters patterned by lithographic techniques, as well as against other masters of interest. Several different techniques are known collectively as soft lithography. They are as described below:

Near-field phase shift lithography. A transparent PDMS phase mask with relief on its surface is placed in conformal contact with a layer of photoresist. Light passing through the stamp is modulated in the near-field. Features with dimensions between 40 and 100 nm are produced in photoresist at each phase edge.

Replica molding. A PDMS stamp is cast against a patterned master. Polyurethane is then molded against the secondary PDMS master. In this way, multiple copies can be made without damaging the original master. The technique can replicate features as small as 30 nm.

Micromolding in capillaries (MIMIC). Continuous channels are formed when a PDMS stamp is brought into conformal contact with a solid substrate. Capillary action fills the channels with a polymer precursor. The polymer is cured and the stamp is removed. MIMIC is able to generate features down to 1 µm in size.

Microtransfer molding (TM). A PDMS stamp is filled with a prepolymer or ceramic precursor and placed on a substrate. The material is cured and the stamp is removed. The technique generates features as small as 250 nm and is able to generate multilayer systems.

Solvent-assisted microcontact molding (SAMIM). A small amount of solvent is spread on a patterned PDMS stamp and the stamp is placed on a polymer, such as photoresist. The solvent swells the polymer and causes it to expand to fill the surface relief of the stamp. Features as small as 60 nm have been produced.

Microcontactprinting ((CP). An "ink" of alkanethiols is spread on a patterned PDMS stamp. The stamp is then brought into contact with the substrate, which can range from coinage metals to oxide layers. The thiol ink is transferred to the substrate where it forms a self-assembled monolayer that can act as a resist against etching. Features as small as 300 nm have been made in this way.

Techniques used in other groups include micromachining of silicon for micro-electrical-mechanical systems (MEMS), and embossing of thermoplastic with patterned quartz. Unlike conventional lithography, these techniques are able to generate features on both curved and reflective substrates and rapidly pattern large areas. A variety of materials could be patterned using the above techniques, including metals and polymers. The methods complement and extend existing nanolithographic techniques and provide new routes to high-quality patterns and structures with feature sizes of about 30 nm. Applications of soft lithography could allow optical devices, such as polarizers, filters, wire grids, and surface acoustic wave (SAW) devices, to be incorporated in the PWB of the embodiments of the invention.

Standard lithography on silicone wafer or silica glass could also be used to fabricate the devices of the embodiments of this invention. While chambers or channels can be made in the devices, fluidic flow can be controlled by pressure gradient, electrical field gradient, gravity, heat gradient etc. The substrate (solid support) of the PWB of the embodiments of the invention can be inorganic material (e.g., glass, ceramic) or metal (e.g., aluminum). The noble metal coating of the fluid channel could be coated with biomolecules, protein, antibody, nucleic acid, for example, for specific analyte binding.

The fluid channel of the embodiments of the invention could be created using the subtractive process, the additive process, or a combination of the processes mentioned above. For example, an uncapped channel could be created in the prepreg forming an underlayer of a PWB, which could be for example about ⅔ the total thickness of the PWB. Subsequently, by an additive process, copper plated with gold could be deposited in the channel. This gold-plating is to prevent direct contact of the copper with a biological fluid flowing through the channel. Next, a matching trace of gold-coated copper layer can be added to the prepreg forming a caplayer of the PWB. The caplayer could be placed on the underlayer, thereby closing the channel with the cap of the channel. Finally, the prepreg is added in the autoclave and cured to form the PWB having a closed fluid channel. This process creates a gold-coated, copper channel in the PWB as shown in FIG. 1.

The advantages of the closed fluid channel of the embodiments of the invention are the following:
(1) Corrosion prevention—The salts from a biofluid flowing through the fluid channel are not allowed to migrate through the cured prepreg matrix of the PWB, thus preventing corrosion or short-circuiting through the PWB.
(2) Greater circuit density—Much less space used due to improved and uniform component spacing and simplified wiring.
(3) Quicker assembly time—Most wiring is already in place. Thus, all one has to do is insert the components and solder in place.
(4) Allows the use of automatic assembly equipment using auto insertion machines wave soldering.
(5) Less room for error—Because generally all the wiring is already determined and in place within the PWB, no additional wiring other than the wiring to connect the PWB to an external device might be required.
(6) Endures shock and vibration—As the PWB contains a closed fluid channel integrally built within the PWB, the PWB is less prone to likely leakage of a fluid flowing the PWB even under strenuous conditions such as shock and vibration.
(7) Ease in troubleshooting—The detection, location, access and removal of a component or a fluid channel within the PWB is easier due to standardized construction of the PWB. Also, components and the fluid channels are physically supported in most cases by their bodies, not leads, and components are soldered together via printed wiring paths instead of wire leads.

The manufacture of the PWB of the embodiments of the invention, wherein the PWB contain a closed fluid channel, would generally start with the preparation of layout drawings or component placement and routing drawings. These preliminary drawing could be used for arranging the components, the fluid channels and their interconnecting patterns for the physical configuration of the board. The preliminary drawings could be rough sketch—not always to exact scale.

Next one would generally need to develop computer-aided-design (CAD) drawings, often referred to as artwork drawings or master pattern drawings, which are scaled to size. The artwork drawings include pads or donuts for component leads and wires and wiring pattern for foil traces.

Then, one would generally need board detail drawing or master drawings, which are drawing used for documenting how the printed circuit board is to be produced. These drawings identify the size and shape of the board, location of all channels and holes (e.g., vias), and the size of all the channels and holes. The notes on the master drawings should preferably define the board material (such as fiberglass epoxy, 1/16" thick with 1 oz. copper on one side), the plating instructions, packaging instructions, and any tolerances allowed.

Next one would generally need marking drawings or silk screen drawing. The purpose of the marking drawings is to indicate what (if anything) is to be printed on the component side of the printed circuit board. Items included in these drawings are circuit name, company name/logo, PWB part number, component outlines, terminal identification, and many other items associated with the printed circuit board.

Finally, one would generally require assembly drawings. The printed circuit board assembly drawings depict the completed board and the location and mounting of all electronic, electromechanical, and mechanical components; including clamps, clips, or other component retaining devices, besides depicting all of the fluid channels though the PWB. These drawings are generally used to document how the PWB is to be assembled. It is usually drawn to scale and viewed from the component side. At times, supplemental views or sections may be necessary to show additional dimensions, part locations, part orientation, or assembly sequence.

Figure 2:
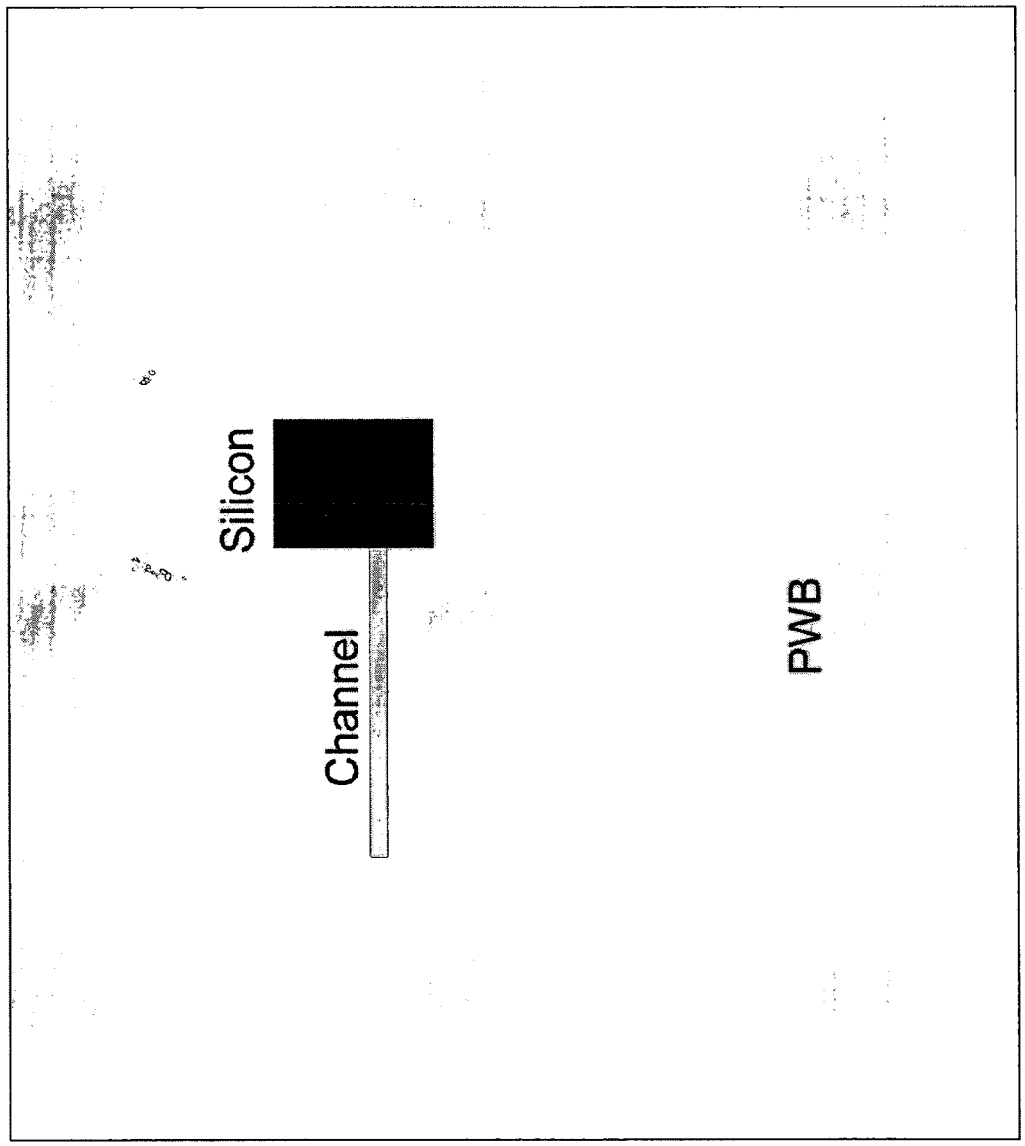
FIG. 2. shows a top view of a PWB of the embodiments of the invention wherein a fluid channel is connected to a device.

The PWB of the embodiments of the invention could include a hole and a fluid channel, which could be made by a process which is subtractive, additive or combination thereof. The PWB having a hole and a fluid channel could further include a bioactive MEMS device such that a biofluid drop could be placed on the top of the hole to deliver the biofluid to a device such as a MEMS device or a microchip as shown in FIG. 2. The PWB of the embodiments of the invention could further include a silicon layer such that the biofluid drop could be placed on the top of the silicon layer for delivering the biofluid to the device such as a MEMS device or a microchip shown in FIG. 2. In other embodiments of the invention, the PWB could incorporate multiple channels and multiple devices such that the PWB can deliver the biofluid to two or more devices, as shown in FIG. 3.

Figure 3:
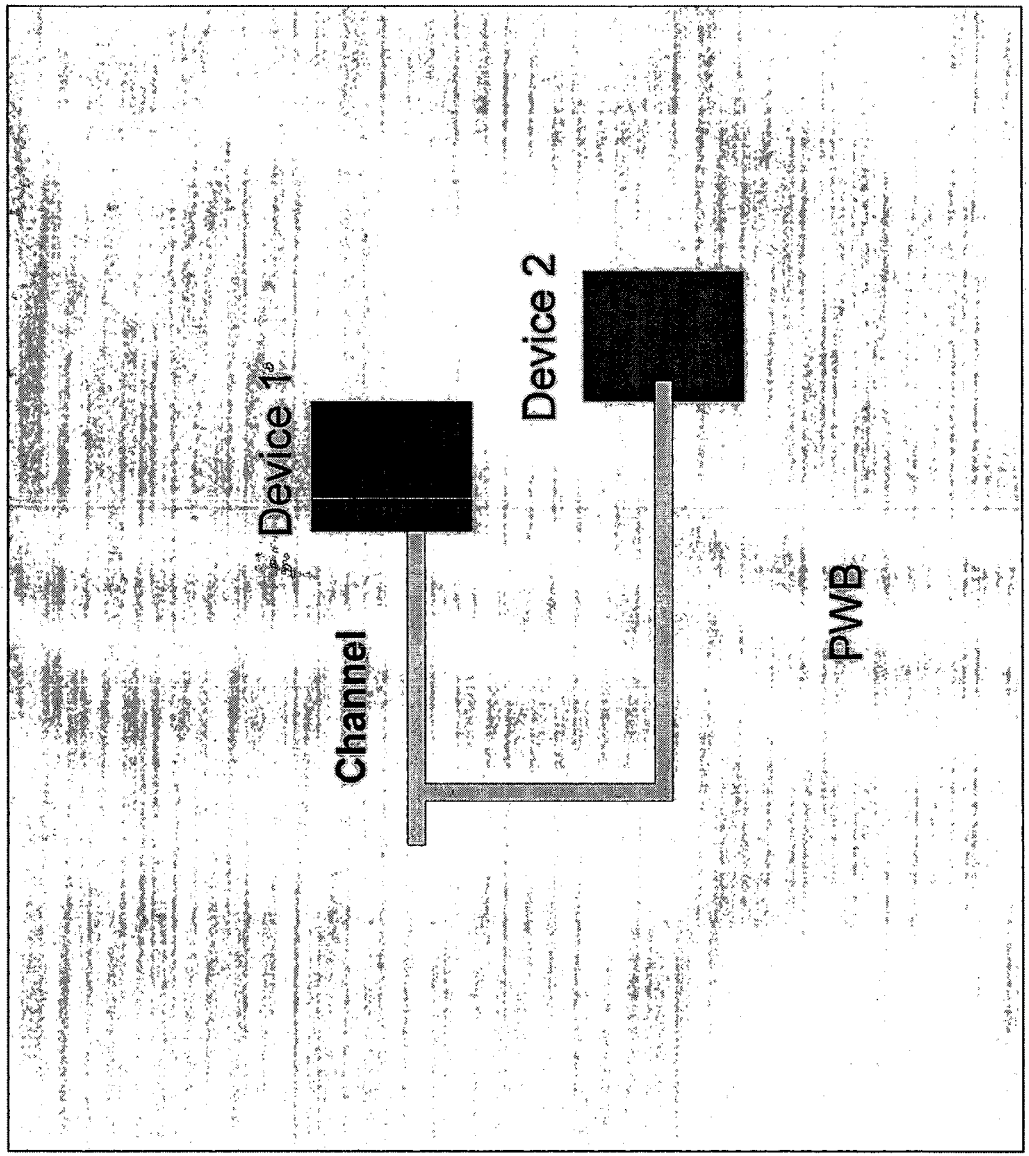
FIG. 3 shows a top view of a PWB of the embodiments of the invention wherein a plurality fluid channels connected a plurality of devices.

While the embodiments of FIGS. 2 and 3 indicate that the one or more devices are integrally incorporated within the PWB, other embodiments of the invention could have some or all of the one or more devices external to the PWB such that the external device is not integrally incorporated within the PWB.

Another embodiment of the invention relates to a PWB for biofluid analysis, wherein the PWB could contain the fluid channel comprising a plurality probes immobilized on spots in the fluid channel or in a device that is connected to the fluid channel. The fluid channel could comprise an inorganic support and an optically transparent cover and further comprises a plurality of probes (i.e., binding partners) optionally with COINs or magnetic COINs immobilized on spots in the fluid channel. The binding partner immobilized on the spot could be attached to an analyte, which in turn could be attached a reporter such as a COIN or a magnetic-COIN.

The PWB of embodiments of the invention could include a silicon biochip and use silicon technology to fabricate interconnects for the silicon biochip to enable on-die synthesis of polymers such as DNA, peptides, and DNA-functionalized complementary nucleotide. Optionally, the embodiments of the invention could use wafer processing cluster tools (process instruments) for synthesis. Typically, in volume silicon processing, a manufacturing line has a cluster of instruments (several identical instruments). Each can support a process step or multiple process steps. By the embodiments of the invention, polymer synthesis can be treated as another process step in a device manufacturing line. A cluster of instruments can be configured within a facility to perform wafer level synthesis for efficient high volume manufacturing.

The devices of the embodiments of the invention may be formed by any suitable means of manufacture, including semiconductor manufacturing methods, microforming processes, molding methods, material deposition methods, etc., or any suitable combination of such methods. In certain embodiments one or more of the electrodes and/or the pad may be formed via semiconductor manufacturing methods on a semiconductor substrate. Thin film inorganic coatings may be selectively deposited on portions of the substrate and/or pad surface. Examples of suitable deposition techniques for depositing copper, gold, or any other material include vacuum sputtering, electron beam deposition, electroplating, solution deposition, and chemical vapor deposition.

The PWB of the embodiments of the invention having closed fluid channel could be used for cooling the PWB. As the density of electrical components on a PWB increase with miniaturization, it is becoming increasingly important to the PWB to be able to efficiently dissipate heat generated by the electrical components of the PWB. By the PWB of the embodiments of the invention, it would be possible to cool the PWB by passing a cooling fluid through the PWB similar to passing cooling fluid the engine block of an automobile.

The embodiments of the invention can be used to carry out the synthesis of polymers such as DNA and peptides by feeding a fluid solution through the closed fluid channel of the PWB of the embodiments of the invention to a biochip site for synthesis of polymers on the biochip. For example, any of a variety of reduction/oxidation (redox) reactions may be employed to electrochemically control the localization and pH of a solution on Si-based electrodes to enable the attachment and elongation of polymers. In such methods, the electrical current drives the oxidation of an appropriate molecule at the anode(s) and the reduction of another molecule at the cathode(s) to control the kinetics and stoichiometry of acid-catalyzed organic syntheses on a Si-based circuit. Such methods can also be used to generate high pH (basic) solutions, and to drive any other electrochemical redox reactions known to one skilled in the art that may or may not result in pH changes (e.g., can also be used to generate reactive free radicals).

Another embodiment of the invention is electrochemical detection of the composition of a biofluid by transporting the biofluid through a closed fluid channel of the PWB of the embodiments of the invention to a biochip. These methods could employ measurements of current flow across a DNA monolayer tethered to a circuit on a silicon substrate. Current flow properties proportionately change when the DNA monolayers are bound by an appropriate redox molecule-tagged test DNA or untagged DNA that is co-added with a redox-active molecule that specifically binds double stranded DNA. Enzyme amplification methods can also be incorporated into such assays in order to enhance the electrochemical signal generated by binding events. Note that these methods can also be adapted by one skilled in the art to measure the binding between other molecular species such as between two proteins or a protein and a small molecule.

The PWB of the embodiments of the invention could also be used for therapeutic materials development, i.e., for drug development and for biomaterial studies, as well as for biomedical research, analytical chemistry, high throughput compound screening, and bioprocess monitoring.

Yet another application of the PWB of the embodiments of this invention includes, for example, sequencing genomic DNA by the technique of sequencing by hybridization. Non-biological applications are also contemplated, and include the production of organic materials with varying levels of doping for use, for example, in semiconductor devices. Other examples of non-biological uses include detection and analysis of anticorrosives, antifoulants, and paints.

It is specifically contemplated that the PWB and/or the methods of manufacturing the PWB of an embodiment of the invention could be used for developing new materials, particularly nanomaterials for many purposes including, but not limited to corrosion resistance, battery energy storage, electroplating, low voltage phosphorescence, bone graft compatibility, resisting fouling by marine organisms, superconductivity, epitaxial lattice matching, or chemical catalysis. Materials for these or other utilities may be formed proximate to one or a plurality of the electrodes in parallel on a plurality of dies of a silicon wafer, for example. Alternatively, materials may be formed by modifying the surface of one or a plurality of electrodes on a plurality of dies by generating reagents electrochemically.

It is further contemplated that an PWB of the embodiments of the invention could be used to develop screening methods for testing materials. That is, reagents electrochemically generated by an electrode on a die could be used to test the physical and chemical properties of materials proximate to the electrode. For example, the PWB could be used for testing corrosion resistance, electroplating efficiency, chemical kinetics, superconductivity, electro-chemiluminescence and catalyst lifetimes.

The advantageous characteristics of some of the embodiments of the invention are illustrated in the examples, which are intended to be merely exemplary of the invention.

The PWB of the embodiments of the invention are preferably PWB built by using silicon process technology and SRAM like architecture with circuitries including electrode arrays, decoders, serial-peripheral interface, on chip amplification, for example.

The embodiments of this invention have several practical uses. For example, one embodiment of the invention allows molecules and nanomaterials detection/analysis based on the electrical readout of specific binding events (target to functionalized electrodes with probes) using CMOS-based devices. Another embodiment of the invention has potential applications for nanomaterials study (for example, in-situ analysis of DNA-mediated assembly of carbon nano-tubes on functionalized electrodes) to be used in electronic devices (CNT transistors and interconnects) as well as well as for detection of bio-species (DNA, protein, viruses etc.) for molecular diagnostics, homeland security, drug discovery and life science R&D work. Yet another embodiment of the invention could be to use Nanomaterials, such as carbon-nanotubes, in potential applications as interconnect materials. Carbon-nanotubes have lower resistivity than Cu and higher electromigration resistance (1000× higher than Cu). Yet another application could be to develop DNA functionalized electrodes with CMOS circuitry for immobilizing, detection, addressing, electrical readout and amplification of the signal can find potential application in silicon DNA chips. The PWB of the embodiments of the invention containing a biochip with DNA functionalized electrodes could find potential application to build nano-structures and in-situ assembly study of nanomaterials. The PWB of the embodiments of the invention containing silicon DNA chips could also find potential application in medical diagnostics, homeland security devices, drug discovery and life science R&D work.

This application discloses several numerical range limitations that support any range within the disclosed numerical ranges even though a precise range limitation is not stated verbatim in the specification because the embodiments of the invention could be practiced throughout the disclosed numerical ranges. Finally, the entire disclosure of the patents and publications referred in this application, if any, are hereby incorporated herein in entirety by reference.

The invention claimed is:

1. A device comprising a printed wire board (PWB) and a biochip, wherein the PWB comprises a fluid channel, the fluid channel is a closed channel comprising a noble metal-containing layer on a surface of the fluid channel, the fluid channel is configured to allow the passage of a fluid, and the biochip is operably attached to the PWB; wherein the PWB further comprises a cured prepreg and the fluid channel is at least partially in the cured prepreg; wherein the fluid channel is entirely enclosed by the noble metal-containing layer.

2. The device of claim 1, wherein the PWB further comprises an integrated circuit.

3. The device of claim 1, wherein the PWB further comprises a microchip.

4. The device of claim 1, wherein the PWB further comprises a semiconductor device.

5. The device of claim 1, wherein the fluid channel is a substantially circular pipe or a substantially rectangular duct.

6. The device of claim 1, wherein the fluid channel has a cross-sectional dimension to permit a biofluid to flow through the fluid channel.

7. The device of claim 1, wherein the fluid channel has a cross-sectional dimension of about 1 micron to about 1.5 cm.

8. The device of claim 1, wherein the fluid channel further comprises copper-containing layer and the noble metal-containing layer comprises gold.

9. The device of claim 1, wherein said surface of the fluid channel is a surface where a fluid that flows through the fluid channel touches the fluid channel.

10. The device of claim 1, wherein the device is a microfluidic device.

11. The device of claim 1, wherein salt in the fluid does not migrate through the PWB.

12. The device of claim 1, wherein the fluid does not short-circuiting the PWB.

13. The device of claim 1, wherein the PWB further comprises a MEMS device and the fluid channel is positioned to permit a fluid to flow through the fluid channel to the MEMS device.

14. The device of claim 1, wherein the fluid channel has at least two openings for fluidic communication.

15. The device of claim 14, wherein the device further comprises an inlet fluid reservoir in fluid communication with at least one of the openings of the fluid channel; and an outlet fluid reservoir in fluid communication with at least one of the openings of the fluid channel.

16. The device of claim 1, wherein the fluid channel is a micro-channel.

17. The device of claim 16, wherein the micro-channel comprises at least one straight segment comprising a cross-section comprising a rectangle.

18. The device of claim 17, wherein the rectangle has a height and a width of between about 1.0 µm and about 500 µm.

19. The device of claim 17, wherein the rectangle has a height and a width of between 10 µm and 50 µm.

20. A method of making the device of claim 1 comprising creating an uncapped channel in the PWB and applying a cap layer on the uncapped channel to form the closed channel.

21. The method of claim 20, wherein the PWB comprises a prepeg.

22. The method of claim 21, wherein the cap layer is a prepreg.

23. The method of claim 21, further comprising curing the prepregs of the cap layer.

24. The method of claim 23, wherein the prepregs comprise a fiber-reinforced thermosetting resin material.

25. The method of claim 20, wherein the PWB comprises a device selected from the group consisting of a biochip, an integrated circuit, a microchip, a semiconductor device, a MEMS device and combinations thereof.

26. The method of claim 20, comprising a subtractive process.

27. The method of claim 26, wherein the subtractive process is selected from a group consisting of a photographic process, a laser ablation process, a screen printing process, and combinations thereof.

28. The method of claim 20, further comprising depositing a metal-containing layer within the uncapped channel.

29. The method of claim 28 wherein the metal-containing layer comprises copper.

30. The method of claim 28, wherein the metal-containing layer comprises a copper-containing layer and a gold-containing layer.

31. The method of claim 28, wherein the metal-containing layer comprises a noble metal.

32. The method of claim 31, wherein the noble metal is selected from the group consisting of gold, silver, tantalum, platinum, palladium and combinations thereof.

33. The method of claim 20, comprising an additive process.

34. The method of claim 20, comprising a combination of a subtractive and additive process.

35. The method of claim 33, wherein the additive process comprises providing the substrate without a conductive plating, fabricating the uncapped channel in the substrate, applying the cap layer on the uncapped channel to form the closed channel, applying a reverse-pattern mask on the substrate or the cap layer, and depositing a conductive pattern.

36. The method of claim 35, further comprising removing a reverse pattern from the substrate or the cap layer.

37. The method of claim 20, comprising a lithography process.

38. The method of claim 37, wherein the lithography process is selected from the group consisting of near-field phase shift lithography, replica molding, micromolding in capillaries, micro-transfer molding, solvent-assisted microcontact molding, microcontact printing and combinations thereof.

39. The method of using the device of claim 1 comprising flowing a fluid through the fluid channel.

40. The method of claim 39, further comprises cooling the PWB.

41. The method of claim 39, further comprising delivering the fluid to a device in the PWB.

42. The method of claim 39, wherein the fluid comprises a biological fluid.

43. The method of claim 39, wherein the biological fluid comprises a salt.

44. The method of claim 42, wherein the noble metal-containing lager substantially prevents migration of the salt through the noble metal-containing lager.

45. The method of claim 39, wherein the noble metal-containing layer comprises a noble metal selected from the group consisting of consisting of gold, silver, tantalum, platinum, palladium and combinations thereof.

46. The method of claim 39, wherein the noble metal-containing layer comprises gold.

47. The method of claim 39, further comprising delivering the fluid to at least two devices in the PWB.

* * * * *